US006323005B1

(12) United States Patent
Daban et al.

(10) Patent No.: US 6,323,005 B1
(45) Date of Patent: *Nov. 27, 2001

(54) TRANSFERRIN-BINDING PROTEIN 1 (TBP1) GENE OF ACTINOBACILLUS PLEUROPNEUMONIAE, ITS USE TO PREPARE PRODUCTS FOR THE UTILIZATION IN VACCINES FOR PLEUROPNEUMONIA AND AS DIAGNOSTIC REAGENTS

(75) Inventors: Montserrat Daban, Barcelona; Enric Espuña, Girona; Andres Medrano; Enrique Querol, both of Barcelona, all of (ES)

(73) Assignee: Laboratorios Hipra S.A., Amer (ES)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/624,655

(22) Filed: Mar. 22, 1996

(30) Foreign Application Priority Data

Mar. 24, 1995 (ES) .................................................. 9500592

(51) Int. Cl.[7] .................................................. C12N 15/09
(52) U.S. Cl. .................. 435/69.3; 536/23.7; 435/69.1; 435/243; 435/252.3; 435/320.1
(58) Field of Search .................. 536/23.1, 23.7, 536/24.32, 24.33; 435/243, 69.1, 320.1, 69.3, 252.3; 424/234.1

(56) References Cited

U.S. PATENT DOCUMENTS 5,417,971 * 5/1995 Potter et al. ........................ 424/256.1

OTHER PUBLICATIONS

R. Beaudet et al. (1994) Protection of mice and swine against infection with *Actinobacillus pleuropneumoniae* by vacinnation Vet. Microbiol. vol. 39, pp. 71–81.
T. Cruijsen et al (1995) Susceptibility to *Actinobacillus pleuropneumoniae* infection in pigs from an endemically infected herd is related to the presence of toxin–neutralizing antibodies. Vet Microbiol. vol. 47 pp. 219–228.
R. Desrosiers (1986) Therapeutic control and economic aspect of porcine *pleuropneumonia* in finishing units. The Vet Record, vol. 119, pp. 89–90.
P. Dom et al. (1992) Comparative virulence of NAD–dependent and NAD–independent *Actinobacillus pleuropneumoniae* strains. J.Vet.Med., vol. 39, pp. 303–306.
P.J. Fedorka–Cray et al. (1990) Efficacy of a cell extract from *Actinobacillus (Haemophilius) pleuropneumoniae* Serotype 1 against Disease in Swine. Infec.Immun. vol. 58, No. 2, pp. 358–365.
L. Fodor et al. (1989) Biochemical and serological properties of *Actinobacillus pleuropneumoniae* biotype 2 strains isolated in swine. Vet.Microbiol. vol. 20, pp. 173–180.

J. Frey et al. (1993) *Actinobacillus pleuropneumoniae* RTX–toxins: uniform designation of haemolysins, cytolysins, pleurotoxin and their genes. J.Gen.Microbiol., vol. 139, pp. 1723–1728.
G.F. Gerlach et al. (1992a) Cloning and expression of a transferrin–binding protein from *Actinobacillus pleuropneumoniae*. Infec.Immun., vol. 60, pp. 892–898.
G.F. Gerlach et al. (1992b) Characterization of two genes enclding distinct transferrin–binding proteins in different *Actinobacillus pleuropneumoniae* isolates. Infec.Immun., vol. 60, pp. 3253–3261.
T.J. Inzana et al. (1988) Virulence properties and protective efficacy of the capsular polymer of *Haemophilus (Actinobacillus) pleuropneumoniae* serotype 5. Infec.Immun., vol. 56, pp. 1880–1889.
M. Legrain et al. (1993) Cloning and characterization of *Neisseria meningitidis* genes enclding the transferrin–binding proteins Tbp1 and Tpb2. Gene, vol. 130, pp. 73–80.
J.I. MacInnes et al. (1987) Analysis of major antigens of *Haemophilus (Actinobacillus) pleuropneumoniae* and related organisms. nfect.Immun., vol. 55, pp. 1626–1634.
J. Nicolet et al. (1992) Diseases of swine. Iowa State University Press, Ames, IA pp. 401–408.
V.J. Rapp et al. (1986) Outer membrane protein profiles of *Haemophilus pleuropneumoniae*. Infect. Immun, vol. 25, pp. 414–420.
A.B. Schryvers et al. (1990) Receptors for transferring in pathogenic bacteria are specific for the host's proteion. CanJ. Microbiol., vol. 36, pp. 145–147.
J.F. vanden Bosch et al. (1990) Heterologous protection induced by an *A. pleuropneumoniae* subunit vaccine. Proceedings of the 11th International Pig Veterinary Society Congress, Lausanne, Switzerland, p. 11.
J.F. van den Bosch et al (1992) Protection induced by a trivalent *A. pleuropneumoniae* subunit vaccine. Proceddings of the 12th International Pig Veterinary Society, The Hague, Netherlands, p. 194.
Gonzalez et al. 1995. Microbiology. 141:2405–2416.*
Querol, E. Submitted May 19, 1995. Public donain Jun. 1, 1995.*
Schryvers et al. Submitted Oct. 18, 1994. Public donain Nov. 13, 1995.*
Wilke, M. Submitted Sep. 19, 1995.*
Gerlach et al. Infect.Immun. 1992.60:3253–3261.*

* cited by examiner

*Primary Examiner*—Jennifer E. Graser
(74) *Attorney, Agent, or Firm*—Henderson & Sturm LLP

(57) ABSTRACT

The present invention relates to the gene of transferrin-binding protein 1 (Tbp1) of *Actinobacillus pleuropneumoniae*, its use to prepare products for vaccination against porcine pleuropneumonia and as diagnostic reagents. The invention also relates to the use of Tbp1 or fragments thereof to produce monoclonal or polyclonal antibodies to be used in diagnostic kits. The invention also relates to the use of Tbp1 or fragments thereof, alone or combined to other virulence factors of the pathogen, as vaccination products against porcine pleuropneumonia.

7 Claims, 4 Drawing Sheets

TRANSFERRIN-BINDING PROTEIN 1 (TBP1) GENE OF ACTINOBACILLUS PLEUROPNEUMONIAE, ITS USE TO PREPARE PRODUCTS FOR THE UTILIZATION IN VACCINES FOR PLEUROPNEUMONIA AND AS DIAGNOSTIC REAGENTS

1. FIELD OF THE INVENTION

The present invention relates to the gene encoding the transferrin-binding protein 1 (thereafter "Tbp1") from *Actinobacillus pleuropneumoniae*. The invention also relates to recombinant plasmids comprising the gene, expression systems for the gene, the use of either the expressed Tbp1 or its antigenic fragments for the formulation of vaccines against porcine pleuropneumonia. Either Tbp1 or fragments thereof can be used with other purposes, such as eliciting antibodies and preparation of diagnostic reagents to disease.

2. BACKGROUND OF THE INVENTION

Porcine Pleuropneumonia

*Actinobacillus pleuropneumoniae* (thereafter "App") is a Gram-negative bacteria which causes porcine pleuropneumonia, a world-wide distributed infectious disease responsible for great economic losses in the swine industry (Nicolet, J., 1992. In: Leman, A. D., Straw, B., Mengeling, W. L., D'Allaire, S., Taylor, D. J., Eds. *Diseases of swine*. Ames, Iowa State University Press, pp. 401–408).

On the basis of β-nicotine-adenine dinucleotide requirements (thereafter "NAD"), App can be divided into biotype 1, NAD-dependent strains and biotype 2, NAD-independent strains. So far, 12 serotypes have been described in biotype 1 being serotype 5 often subdivided into 5a and 5b (Nielsen, R., 1986. *Acta Vet Scand*. 27, 453–455), and 2 serotypes in biotype 2 (Fodor, L., Varga, J., Molnar, E. and Hajtos, I., 1989. *Vet. Microbiol*. 20: 173–180). Serotyping is mainly based on capsular antigens.

The virulence of the agent seems to be more or less related to the serotype, although all App serotypes described in both biotypes may cause the disease and death in pigs. Biotype 2 strains show less virulence than those of biotype 1, and field observations indicate that serotypes 1, 5a, 5b, 9 and 10 are more virulent than the other biotype 1 serotypes (Dom, P. and Haesebrouck, F., 1992. *J. Vet. Med. B*., 39: 303–306).

The main route of App spread is airborne and the disease is transmitted mainly by direct contact from pig to pig or by droplets within short distances. In acute outbreaks the infection may jump from one pen to another, suggesting the possible role of aerosols in connection with long distances or the indirect transmission of contaminated exudate by farm personnel. It is generally accepted that App enters the pulmonary alveoli directly via the trachea and bronchi. The clinical signs of porcine pleuropneumonia vary with the state of immunity of the animals, the environmental stress or the degree of exposure to the infectious agent. All age categories may suffer the disease, but young fattening pigs are more frequently affected. The clinical course may be peracute, acute or chronic. In the peracute form, there is an intense inflammatory response, with haemorrhage, edema and fibrinous exudation. The acute form of the disease is characterized by extensive haemorrhage and fibrinous exudation in the pulmonary parenchyma and the pleural cavity, being defined as fibrinous pleuritis and haemorrhagic necrotizing pneumonia that causes the death of the animal within a period of 24–48 hours. Pigs that survive the disease may become carriers of the pathogen, and develop chronic injuries as pulmonary necrosis, nodules and fibrinous adherences in the pleural cavity. Other signs are lack of appetite and decreased gain in body weight (Nicolet, 1992).

Economic losses due to acute outbreaks of the disease result mainly from the high mortality (1–10% or more) and costs for medication (Desrosiers, R., 1986. *Vet. Rec*. 119: 89–90). Economic losses resulting from chronic cases of pleuropneumonia are due to a decreased growth rate of the affected animals.

Virulence Factors or App

Capsule

All App strains possess an oligosaccharide capsule that protects the agent from phagocytosis and complement lysis. This structure seems to contribute to the agent virulence and may play a role in serotype-specific partial protection induced by vaccination with bacterins.

Lipopolysaccharides

Lipopolysaccharides (thereafter "LPSs") are the main constituents of the outer membrane of Gram-negative bacteria. They consist of a polysaccharide and a lipid A moiety, the latter being an endotoxin. Purified App LPSs induce non haemorrhagic nor necrotic lesions in pig lungs, which indicate that LPSs are not responsible for the typical App lesions, but may contribute to their formation (Jansen, R., 1994. PhD Thesis, Utrecht, The Nederlands).

Outer-membrane Proteins

Convalescent animal sera recognize several proteins from the outer membrane of App (thereafter "OMPs"). Some of them, specifically induced under iron restriction, will be discussed further. OMP electrophoretic profiles differ for most serotypes of App (Rapp, V. J., Munson, R. S. and Ross, R. F., 1986. *Infect. Imm*. 52: 414–420), although three proteins of 17, 32 and 42 kilodaltons (thereafter "kDa") are immunologically dominant (Macinnes, J. I. and Rosendal, S. 1987. *Infect. Imm*. 55: 1626–1634). Immunization with a crude extract of outer membranes conferred a limited protection to the challenge with the pathogen (Beaudet, R., McSween, G., Boulay, G., Rousseau, P., Bisaillon, J. G., Descoteaux, J. P. and Ruppaner, R. 1994. *Vet. Microbiol*. 39: 71–81).

Transferrin-binding Proteins

Iron is essential for bacterial growth. However, it is complexed to the host glycoproteins transferrin and lactoferrin in the extracellular environment. Thus, the pathogenic bacteria have developed different strategies to acquire this element. Several Actinobacillus, Haemophilus and Pasteurella species have shown to possess a mechanism of iron acquisition involving direct binding of the hosts transferrin by receptor proteins on the surface. Those receptors are only expressed under iron restriction conditions. They consist of two distinct proteins, Tbp1 and Tbp2, specific for host's transferrin. Tbp1 proteins are probably transmembrane proteins that serve as channels for transport of iron across the outer membrane, while Tbp2 seem to be lipoproteins anchored to the outer membrane by their N-terminal lipid tail. Schryvers (Schryvers, A. B. 1994. Abstracts Haemophilus, Actinobacillus and Pasteurella International Conference, Edinburgh, UK, 23–24) suggested an iron acquisition pathway involving the binding and removal of iron from transferrin at the bacterial surface by the coordinate action of Tbp1 and Tbp2, followed by a transport of iron across the outer membrane via Tbp1 and binding of iron by a periplasmic binding protein.

Three other Tbp proteins, of 60, 62 and 65 kDa, have been identified among App serotypes. Immunization of pigs with the 60-kDa Tbp conferred limited protection to the challenge with homologous strains (Gerlach, G. F., Anderson, C., Potter, A. A., Klashinsky, S. and Wilson, P. J. 1992. *Infect. Imm.* 60: 892–898).

Proteases

App secretes proteases that degrade porcine gelatin, immunoglobulin A (thereafter "IgA") and haemoglobin (Negrete-Abascal, E., Tenorio, V.R., Serrano, J. J., Garcia, C., de la Garza, M. 1994. *A. Can. J. Vet Res.* 58: 83–86). It has been suggested that the cleavage of IgA by proteases could facilitate the mucosal spread of App, and that proteolysis of haemoglobin could be a mechanism of iron acquisition.

RTX toxins

Two haemolytic RTX exotoxins (I and II) and one cytolytic, non haemolytic RTX exotoxin (III) have been described among the different App serotypes (Frey, J., Bosse, J. T., Chang, Y., Cullen, J. M., Fenwick, B., Gerlach, G. F., Gygi, D., Haesebrouck, F., Inzana, T. J., Jansen, R., Kamp, E. M., Macdonald, J., MacInnes, J. L., Mittal, K. R., Nicolet, J., Rycroft, A., Segers, R. P. A. M., Smits, M. A., Stenbaek, E., Struck, D. K., van den Bosch, J. F., Willson, P. J. and Young, R. 1993. *J. Gen. Microbiol.* 139: 1723–1728). They belong to the pore-forming RTX-toxin family (repeat-in-the-toxin), widely spread among pathogenic Gram-negative bacteria. These exotoxins are toxic for porcine alveolar macrophages and neutrophils.

The protection conferred by these toxins against porcine pleuropneumonia has been demonstrated by immunization of pigs with RTX combined to other bacterial components (Beaudet et al., 1994). However, it has also become clear that RTX are not the only factors involved in immunity.

Vaccination

Economic losses resulting from porcine pleuropneumonia place this disease among the most important ones in swine. However, current vaccination methods do not confer a complete protection against all App serotypes.

Vaccination with bacterins, prepared from whole cells of different serotypes (Inzana, T. J., Ma, J., Workman, R. P., Gogolewski, P. and Anderson, P. 1988. *Infect. Imm.* 56:1880–1889), chemically inactivated and adjuvanted with aluminum hydroxide may provide immunity against bacteria, but not necessarily against the products secreted by them, involved in pathogenesis.

LPSs, responsible for serotype specificity, are bad immunogens and combinations of LPSs and OMPs provide a protection degree comparable to bacterins (Inzana et al., 1988).

Vaccination assays with extracts obtained from culture supernatants allow for a protection against App that results more effective than immunization with bacterins. This fact demonstrated the importance of secreted factors, particularly the RTX exotoxin I (Fedorka-Cray, P. J., Hueter, M. J., Stine, D. L. and Anderson, G. A.,1990. *Inf Imm.*, 58: 358–365).

Van den Bosch and col. (Van den Bosch, J. F., Pennings, A. M. M. A., Cuijpers, A. N. B., Pubben, A. N. B., van Vugt, F. G. A. and Van der Linden, M. F. I., 1990. *Proceedings of the 11th International Pig Veterinary Society Congress*, Lausanne, Switzerland, p. 11; Van den Bosch, J. F., Jongenelen, I. M. C. A., Pubben, N. B., van Vugt, F. G. A. and Segers, R. P. A. M., 1992. *Proc. 12th International Pig Veterinary Society Congress*, The Hague, The Netherlands, p. 194) have suggested the use of vaccines by subunities, prepared from a combination of RTX and OMPs. Those preparations allowed a complete protection of the animals from mortality and development of lung lesions.

3. SUMMARY OF THE INVENTION

The present invention relates to the selection and cloning of fragments enclosing the nucleotide sequence of the gene encoding the protein Tbp1 of *Actinobacillus pleuropneumoniae*.

The present invention also encompasses the set of recombinant prokaryotic vectors that comprise fragments of the sequence of the gene encoding Tbp1 of App, as well as cells carrying these vectors.

The present invention also relates to the methods for the production of recombinant Tbp1 of App or antigenic polypeptides thereof, which involve: growth of cells carrying the recombinant expression plasmids that contain fragments of the gene of protein Tbp1 operably linked, expression of these sequences under the required conditions, and further purification of the fragments expressed.

A further aspect of the invention entails antibodies obtained by immunization of animals with antigenic polypeptides produced by expression of recombinant plasmids containing operably linked fragments of the gene encoding Thp1 of App.

The invention also encompasses the utilization of the antibodies elicited against Tbp1 in App diagnostic systems or in serotherapy.

It is also an aspect of the invention the use of the recombinant Tbp1 or antigenic polypeptides thereof to prepare an universal vaccine against porcine pleuropneumonia.

The present invention encompasses the use of the recombinant Tbp1 or the antigenic fragments thereof, as diagnostic reagents to App.

The invention finally encompasses the use of either the Tbp1 gene or fragments thereof as diagnostic reagents.

4. DETAILED DESCRIPTION OF THE INVENTION

The objectives of the present invention have been achieved by cloning, sequencing and expressing the DNA fragments comprising the sequence of the Thp1 gene from App.

The objectives described have been achieved in the preferred form of the invention as follows:

(1) Selection of a suitable probe for the identification of the gene encoding Tbp1 within the App genome.

(2) Cloning and sequencing of those fragments comprising the sequence of the Tbp1 gene from App.

(3) Insertion in frame of the gene or fragments thereof encoding the Tbp1 protein into appropriate expression vectors, and expression of the protein or fragments of it in suitable hosts.

In the preferred form of the present invention, the expression of either Tbp1 or fragments thereof was achieved by using fusion vectors of cytoplasmic expression (as pMAL™-c2, New England Biolabs, Beverly, USA).

In other forms of the present invention other expression vectors may be used, as pET-22b(+) (Novagen, AMS Biotechnology, USA) (Rebordosa. X., Piñol, J., Pérez-Pons, J. A., Lioberas, J., Naval, J. and Querol, E. 1994 Gene 149: 203–209), pGem®-3Z (Promega Corporation, USA), vectors that fuse the expressed fragments to other proteins, as β-galactosidase (pEX and pXa, Boehringer Mannheim Espa na, S.A.) and vectors for other host types or vectors for prokaryotic expression (Bacillus, Streptomyces, etc.) and eukaryotic expression (yeast, baculovirus, etc.), with several easy-to-use variants, useful to researchers having general skills on recombinant DNA techniques.

In the preferred form of the present invention, protein Tbp1 was obtained from crude *Escherichia coli* cell extracts upon purification of the protein or expressed fragments thereof through amylose-resin columns.

The purification of some of the Tbp1 fragments expressed in the present invention has also been obtained from the periplasmic fractions of the induced cultures. Since purifications from whole intracellular extracts yield a higher amount of protein, only these procedures have been considered in the preferred form of the invention. Some of the systems used involve affinity-based purifications other than amylose-resin columns, for instance β-galactosidase fusion-based systems. In these cases, either p-amino phenyl-β-D-thyogalactoside columns (Ullman, A. 1984. Gene, 29: 27–31) or resins containing immobilized divalent cations, as His•Bind™ Resin (Novagen, AMS Biotechnology, USA) were used, as well as affinity chromatographies based on the binding specificity of Tbp1 to porcine transferrin.

In the present invention, antibodies raised against the different polypeptide fragments were obtained upon immunization of New Zealand rabbits and purification from immune sera.

The method employed is not critical for the obtention of these antibodies. For instance, they may be obtained using mineral-oil-based adjuvants, aluminum hydroxide or any substance producing a stimulation of the immune response in a non specific way. Also, immunization patterns different from those described in the preferred form of the invention may be applied, as well as other immunization pathways (intramuscular, intradermal, intravenous or any combination of them). In other forms of the invention, animals other than rabbits can be used, such as mice, rats, hamsters, guinea-pigs or hens, for the raising of specific antibodies. The obtention of sera from those animals may also be done by processes different from those described in the preferred form of the invention (for instance, total exanguination or direct heart puncture).

In another form of the invention, antibodies may be obtained upon immunization of mice and monoclonal antibodies production and purification. These monoclonal antibodies may be selected by their affinity to the different fragments expressed or by their affinity to *Actinobacilus pleuropneumoniae* extracts.

In another preferred form of the invention, purified Tbp1 was used to prepare an universal vaccine by subunities against porcine pleuropneumonia. With this aim, the protein was combined and emulsified with Markol® and aluminum hydroxide. Also, in another form of the invention, the purified Tbp1 protein was emulsified with a mixture of lipids and phospholipids for the preparation of liposomes. In other forms of the invention, oily adjuvants as Drakeol® or non-oily adjuvants as saponines and aluminum hydroxide, may be used. Also, a presentation system as ISCOMS may be employed. All the process can suffer a number of variations, and it will not represent any problem to experienced researchers with skills on this field.

DETAILED DESCRIPTION OF THE FIGURES

FIG. 1 shows the cloning of the gene encoding Tbp2 of App into the polycloning site of the plasmidic vector pUC119. The gene encoding Tbp2 of App, serotype 1, is flanked by the sites for the restriction enzymes (thereafter "REs") Nsi I and Kpn I. The gene is cleaved from genomic DNA of App, serotype 1, with both REs and ligated to pUC119, between the sites for the REs Pst I (compatible ends with Nsi I) and Acc 65 I (isosquizomer of Kpn 1). The resulting 5 021 bp recombinant plasmid is named pTR2.1370, and the Tbp2 gene sequence comprised in it is used as a probe for the detection and identification of the gene of the Tbp1 protein of App, serotype 1. The shaded box in the figure indicates the Tbp2 gene. The Acc 65 I site is located 116 nucleotides downstream of the end of the gene.

In FIG. 2A the recombinant plasmid pTR1a2.1370 is shown. This plasmid contains the complete sequence of Tbp2 and 2 202 nucleotides of the Tbp1 gene sequence, which were identified by hybridization of the App genomic DNA, digested with the RE Nsi I, with the Tbp2 gene previously cleaved from pTR2.1370 with the REs Hin dIII and Acc 65 I and radioactively labeled with $^{32}$p. The about 4 000 bp fragment identified was cloned into the Pst I site of pUC119. By cleavage of this plasmid with the RE Acc65 I, nucleotides 113 to 2 212 of Tbp1 gene were liberated and subcloned in the Acc65 I site of pUC119. The resulting plasmid was named pTR1a.1370.

FIG. 2B describes the cloning of the Bgl II-Bgl II fragments (obtained by cleavage of pTR1a2.1370 with this RE) into the Bam Hi site of pUC119. The resulting recombinant plasmid is named pBgl.tr2.

5. EXAMPLE OF THE PREFERRED FORM OF THE PRESENT INVENTION

The objectives of the present invention involve the cloning, sequencing and expression of the gene encoding the Tbp1 of App. The gene or fragments thereof, and the protein or fragments thereof may be used for several purposes; among them are the diagnostic of App and the design of a vaccine by subunities. The invention includes the cloning and sequencing of the gene encoding Tbp1, as well as the expression of the protein from suitable vectors.

*Actinobacillus pleuropneumoniae* strain 1370, derived from strain Hpn-1 (ATCC 27088) of serotype 1 was used for the molecular cloning of the Tbp1 gene. Recommended culture media are prepared as following: per liter, 33 g of tryptose blood agar (Difco 0232-01-9), 1% yeast extract (Difco 0127-01-7), 20 mg of NAD (Sigma N-0632), 1% Chicken serum, 8% lamb blood (solid medium) or 37 g of Brain Heart Infusion BHI (Difco 0037-01-6) and 20 mg of NAD (liquid medium).

Genomic DNA of App was obtained according to Sambrook and col. (Sambrook, J., Fritsch, E. F. and Maniatis, T., 1989. Molecular Cloning. A Laboratory Manual, 2nd. Ed. Cold Spring Harbor Lab. Press), from pellets of cultures grown to $A_{600}=1$.

The invention may be described as follows:

5.A. Selection of a DNA fragment to be used as a probe for the detection and identification of the DNA sequence encoding protein Tbp1 of App.

5.B. Radioactive labeling of the probe. Use of the probe to detect and identify the DNA sequence encoding protein Tbp1 of App.

5.C. Cloning and sequencing of the App Tbp1 protein gene.

5.D. Insertion in frame of the gene encoding Tbp1 into the expression vector pMAL™-c2.

5.E. Assays of expression of the Tbp1 gene in the E. coli strain BL21 (Novagen, AMS Biotecnologfa (Spain), S.L.), according to the procedures specified by the manufacturer.

5.F. Obtention of Tbp1-specific antibodies, being the protein expressed as in 5.E.

5.A. Selection of a DNA Fragment to be used as a Probe for the Detection and Identification of the DNA Sequence Encoding Protein Tbp1 of App.

Figure 1:
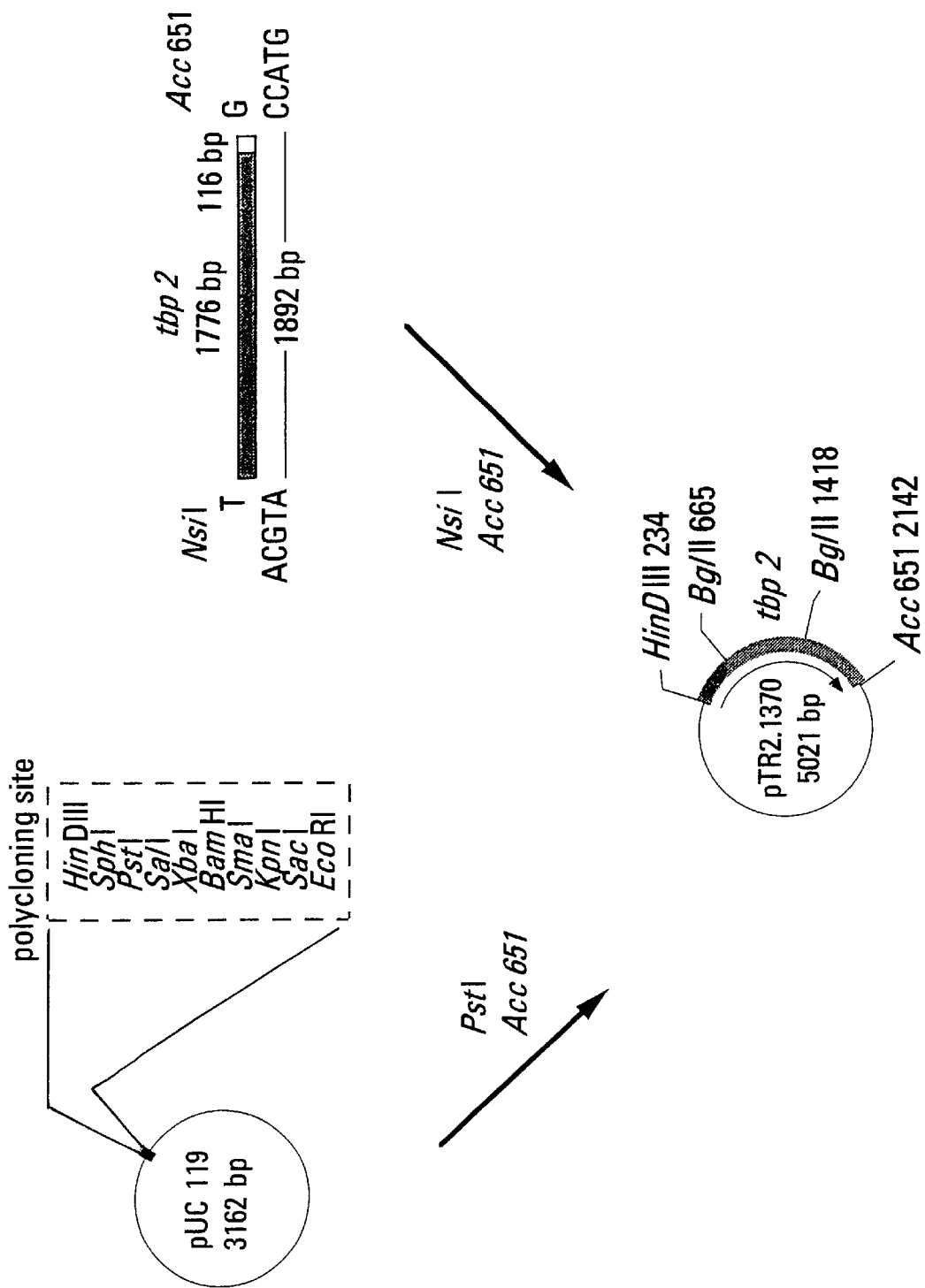

The Gram-negative pathogens possess outer-membrane proteins specific for the host transferrin (Schryvers, A.B. and Gonzalez, G.C. 1989. Can. J. Microbiol. 36:145–147), which take part in a system for iron uptake that exhibits high similarities among the species so far studied. In Neisseria meningitidis, the gene encoding Tbp2 ends 80 bp upstream of the beginning of the Tbp1 gene (Legrain, M., Mazarin, V., Irwin, S. W., Bouchon, B., Quentin-Millet, M. J., Jacobs, E. and Schryvers, A. B. 1993. Gene 130: 73–80). Taking the genomic organization of Neisseria as a model, we assumed that the Tbp1 gene of App is located at a position comparable to that of Neisseria. We have used the published sequence of the gene encoding Tbp2 (Gerlach, G. F., Klashinsky, S., Anderson, C., Potter, A. A. and Willson, P. J. 1992. Infect. Imm. 60, 8: 3253–3261) as a probe. With this aim, and considering that the gene encoding Tbp2 from serotype 1 App is flanked by the RE sites Nsi I and Acc 65 I (see FIG. 1), we performed a complete restriction of App genomic DNA, serotype 1, with both enzymes. Fragments ranging form 1 800 to 2 000 bp (the Nsi I-Kpn I fragment comprising the Tbp2 gene is 1 892 bp long) were recovered from 1% agarose gels run in 40 mM Tris[hydroxymethyl] aminomethane] (thereafter "Tris")-acetate, pH 8.0, (ethylenedinitrilo)tetraacetic acid disodium salt (thereafter "EDTA") (thereafter "TAE").

The fragments selected were cloned into the plasmidic vector pUC119, between the RE sites Pst I (compatible ends with Nsi I) and Acc 65 I. The recombinant plasmids obtained were used to transform Escherichia coli XL1 Blue strain and selected by α-complementation (Sambrook et al., 1989) on LB agar plates supplemented with 50 µg / ml ampicillin, 50 µg/ml isopropylthio-β-D-galactoside (thereafter "IPTG") and 50 µg/mL 5-bromo-4-chloro-3-indolyl-β-D-galactoside (thereafter "X-Gal") (Sambrook et al., 1989). The identity of the recombinant plasmid was confirmed by restriction with the RE Bgl II (see FIG. 1), which generates a 753 bp fragment. Further confirmation of the identity of the fragment was achieved by enzymatic sequencing (Sanger, F., Nicklen, S. and Coulson, A. R., 1977. Proc. NatL Acad. Sci. 74: 5 463), using the T7 sequencing Kit (Pharmacia 27-1682-01). The recombinant plasmid was named pTR2.1370 (see FIG. 1).

5.B. Radioactive Labeling of the Probe. Use of the Probe to Detect and Identify the DNA Sequence Encoding Protein Tbp1 of App.

The fragment containing the sequence of the gene of protein Tbp2 was excised from pTR2.1370 with the RE Hin dIII and Acc 65 I and labeled with α-$^{32}$P(dCTP) with the random priming kit "Prime-a-gene" (Promega U1100).

Figure 2:
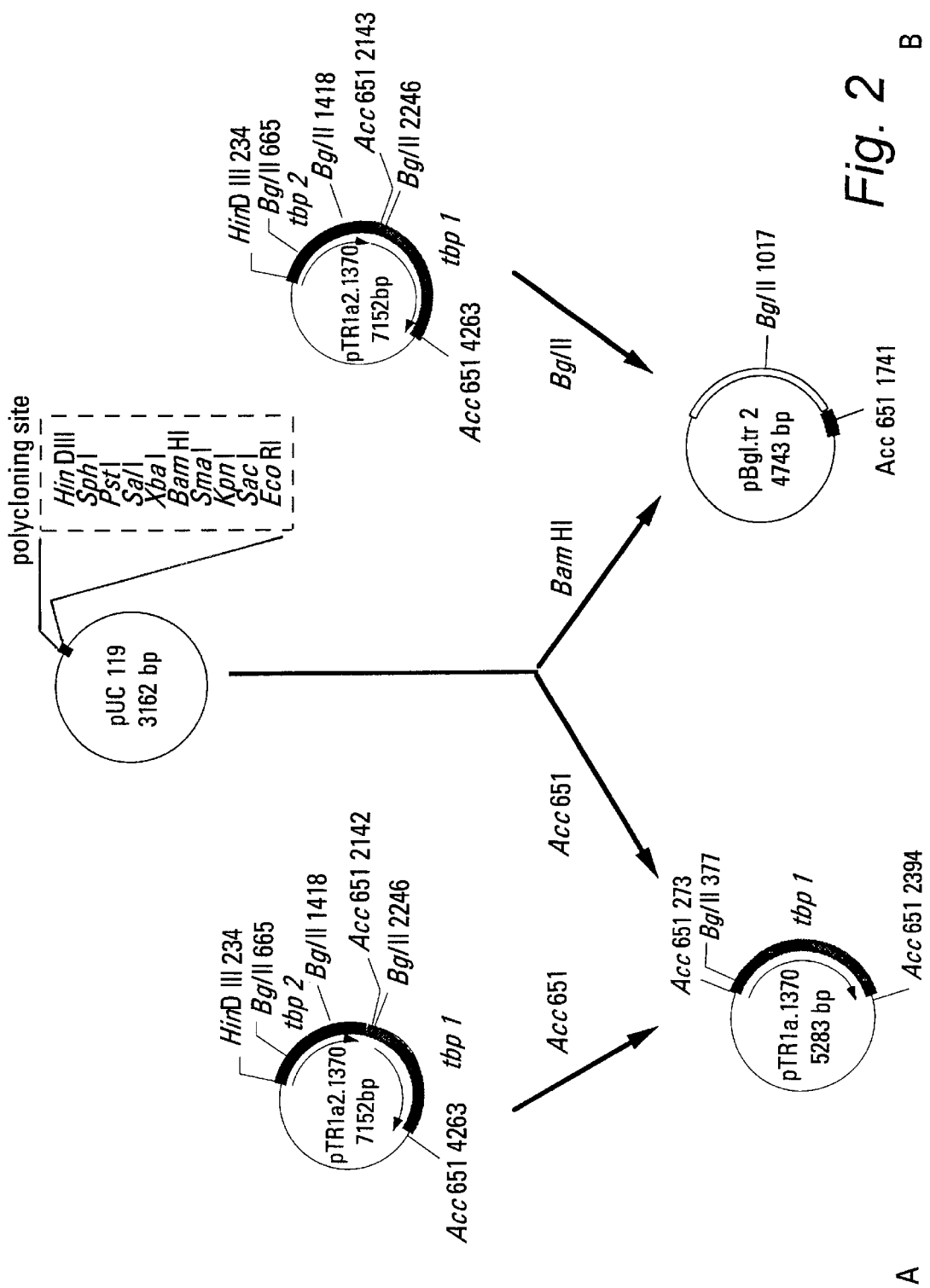

The probe was hybridized with serotype 1 App genomic DNA digested with the RE Nsi I and previously transferred from an 0.8% agarose gel in TAE to a nylon membrane by Southern blotting (Sambrook et al., 1989). A 4 kilobases (thereafter "kb") fragment was detected. A preparative restriction of App serotype 1 genomic DNA was performed with Nsi I, and fragments between 3 500 and 4 500 bp were recovered and cloned in the Pst I site of pUC1 19. Recombinant plasmids obtained were used to transform Escherichia coli XL1 Blue strain. The screening was performed again by restriction with Bgl II, and confirmed by enzymatic sequencing and comparison with the Tbp2 gene sequence published. The recombinant plasmid was named pTR1 a2.1370 (see FIG. 2A).

5.C. Cloning and Sequencing of the APP Tp1 Protein Gene.

5.C.I. Cloning and enzymatic sequencing of a fragment containing nucleotides 11–113 of the Tbp1 gene.

The 753 bp and 826 bp-fragments obtained by Bgl II - Bgl II restriction of the pTR1 a2.1370 insert (see FIG. 2A) were cloned into the Bam HI site of pUC 1 9 (compatible ends). Recombinant plasmids were used to transform E.coli XL1 Blue cells and screened by restriction with Acc 65 I (see FIG. 2B). The recombinant plasmid was named pBgl.tr2 and sequenced with the Universal Primer (Clontech 6420-1), which provided the nucleotide sequence of the first 103 bp of Tbp1.

.5.C.II. Cloning and sequencing of the fragment comprising nucleotides 114-2 212 of the gene of Thp1. identified in 5.B., into the plasmidic vector pUC1 19.

pTR1a2.1370 was digested with Acc 65 I (see FIG. 2A) to liberate the fragment comprised between the sites Acc 65 I of the gene of protein Tbp1 (104 bp downstream of the first nucleotide of the initiation codon) and Acc 65 I of the pUC1 19 polycloning site. The fragment excised was cloned into the Acc 65 I site of pUC119, and the recombinant plasmids were used to transform E.coli XL1 Blue cells. Plasmids were screened by restriction with Bgl II (there is a target for this enzyme 103 bp downstream of the Acc 65 I site, 207 bp from the beginning of the gene; see FIG. 2A). The identity of the fragment cloned was confirmed by enzymatic sequencing. The recombinant plasmid containing the fragment comprised between nucleotides 114 and 2 212 was named pTR1a.1370. The sequencing of the Tbp1 gene fragment comprised in this recombinant plasmid was made with M13 Reverse Primer (Clontech 6430-1) and the following oligonucleotides, designed as specific primers:

| | | |
|---|---|---|
| $O_{303-326}$ | 5' GGGCTTGGCATTAGACGGTTTGCC 3' | (24-mer) SEQ ID NO.3 |
| $O_{460-479}$ | 5' GGCGGTTCGGTGCAATTCCG 3' | (20-mer) SEQ ID NO.4 |
| $O_{586-613}$ | 5' GCGGGTACTCACAATGGCTTTGATGCTC 3' | (28-mer) SEQ ID NO.5 |
| $O_{689-714}$ | 5' CCCGAGTAGGAGTGGAAACCAACAG 3' | (26-mer) SEQ ID NO.6 |
| $O_{918-946}$ | 5' GCGTCTAAATGCTCAGGATTACACTGGTG 3' | (29-mer) SEQ ID NO.7 |
| $O_{1403-1379}$ | 5' CAGTTGTTCTCTCTCAAGCGGGTAG 3' | (25-mer) SEQ ID NO.8 |
| $O_{1766-1747}$ | 5' GTAGCACAATCAGCCCTACC 3' | (20-mer) SEQ ID NO.9 |
| $O_{1892-1872}$ | 5' GCCCAGCGATGAGTGCTACGG 3' | (21-mer) SEQ ID NO.10 |

Figure 3A:
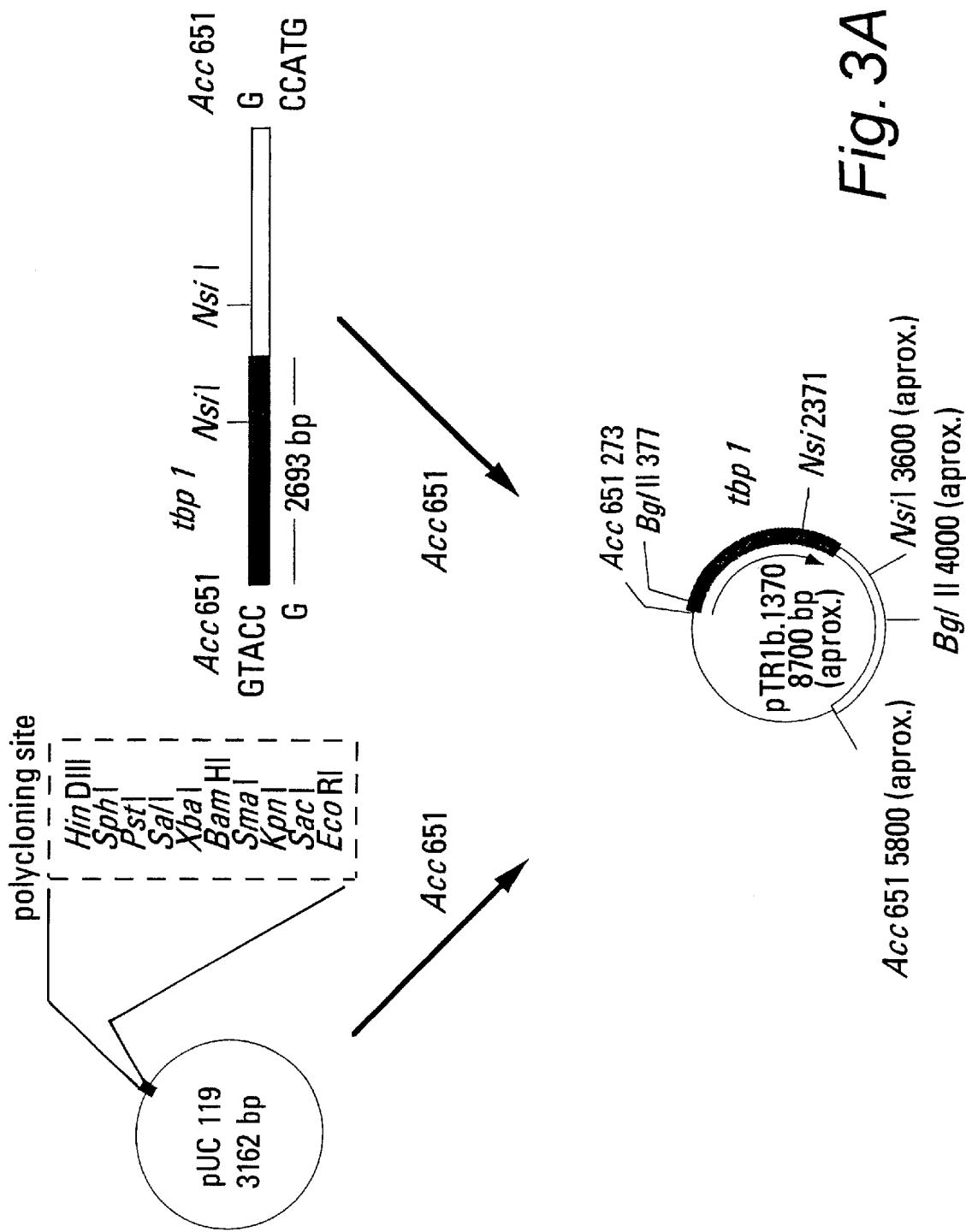
FIG. 3A shows the recombinant plasmid pTR1b.1370, which contains the fragment of the Tbp1 gene comprising nucleotides 114-2 803, cloned in the site for the RE Acc 65 I of pUC119.

5.S.C. III. Use of the fragment 114-2 212 as a probe to detect the fragment 2 213-2 803 of the gene of Tbp1. Cloning and sequencing of the 2 213-2 803 fragment of the Tbp1 gene pTR1a.1370 was cleaved with the RE Acc 65 I to liberate the 114-2 212 fragment of Tbp1 (see FIG. 2A). This fragment was radioactively labeled as previously detailed in 5B (for the labeling of another fragment), to be used as a probe to detect and identify the complete sequence of Tbp1 gene. App genomic DNA digested with Acc 65 I, transferred to a nylon membrane by Southern blotting and hybridized to the probe. A 5.6 kb fragment was detected and cloned into pUC119 Acc 65 I site. Recombinant clones were used to transform E. coli XL1 Blue cells and screened by restriction with Acc 65 I and Nsi I (see FIG. 3A). The recombinant plasmid was named pTRl b.1370. Sequencing of the 2 212-2 803 fragment of the Tbp1 gene was performed using the following oligonucleotides as specific primers:

$O_{1949-1975}$ 5' CGTCATTCCTATCGCTCTCTTATCGAG 3' (27-mer) SEQ ID NO.11

$O_{2425-2450}$ 5' GTTGTAGGAGTGGGGTACTATCAGCC 3' (26-mer) SEQ ID NO.12

Figure 3B:
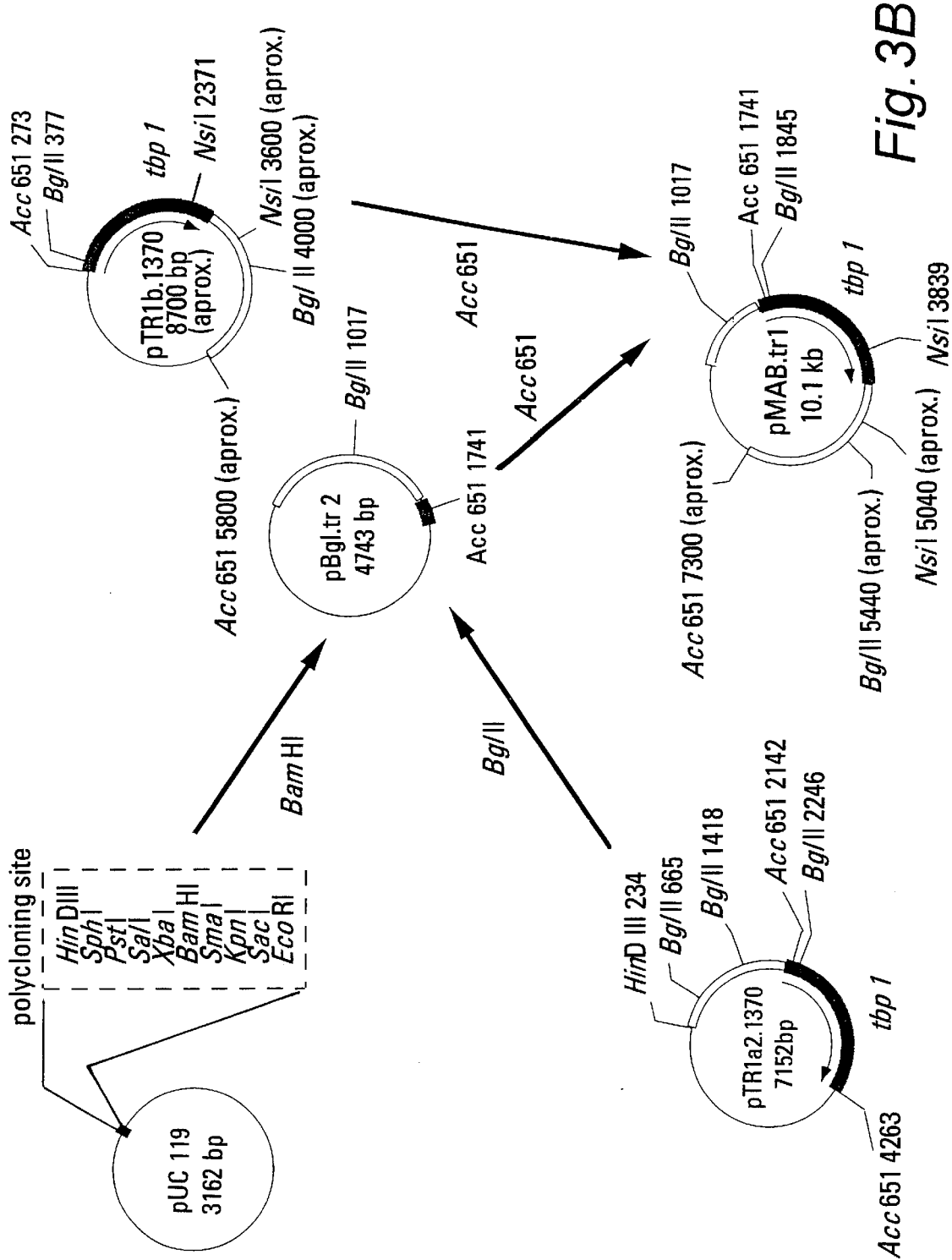
FIG. 3B shows the construction of the recombinant plasmid pMAB.tr1 containing the complete nucleotide sequence of the gene of Tbp1 of App, serotype 1.

The fragment comprising the complete sequence which codes for the Tbp1 protein was excised from the recombinant plasmids pBgl.tr2 and pTR1 b.1 370 and cloned into pUC119 (see FIG. 3B). The resulting recombinant plasmids called pMAB.tr1 was deposited on Mar. 2, 1995, and has been registered with the number 4548 at the "Coleccion Española de Cultivos Tipo".

5.D. Insertion in Frame of the Gene Encoding Tbp1 into the Expression Vector pMAL™-c2.

A genomic fragment comprising the sequence of the Tbp1 gene encoding the mature protein (nucleotides 77-2 803) and the termination codon (2 804-2 806) was amplified by PCR, with the purpose of inserting the Tbp1 gene into the plasmid pMAL™-c2 in frame.

Primers ex5 and ex3 were designed after the Tbp1 gene sequence (SEQ.ID.No 1), entering the mutations needed to create the sites for the REs Eco RI and Xba I, between which the gene encoding for the mature Tbp1 was to be cloned. Mutations are indicated in boldface on the primer sequences:

SEQ ID NO.13
ex5 5' GCTATGCAGAATTCGCGGTACAATTAAATG 3' (30-mer)

SEQ ID NO.14
ex3 5' GGTACTCTAGATTAGAATTTCATTTC 3' (26-mer)

The resulting recombinant plasmid was named pMAL.tr1. The plasmid yields the expression of a fusion product which contains the maltose-binding protein (thereafter "MBP") and the mature Tbp1 protein. The molecular mass expected for the fusion product is 146.5 kDa.

5.E. Assays of Expression of the Tbp1 Gene in the E. coli Strain BL21.

The E. coli BL21 strain was transformed with the plasmid pMAL.tr1, according to the procedures specified by the manufacturer.

The clones carrying the plasmid with the fusion were cultured for 12 hours in 2xYT medium (per liter: 16 g of tryptone, 10 g of yeast extract and 5 g of NaCl), supplemented with 100 µg/ml of ampicillin. Each culture was inoculated in 100 ml of rich medium (per liter: 10 g of tryptona, 5 g of yeast extract and 5 g of NaCl), supplemented with 2g/l of glucose and 100 µg/ml of ampicillin, allowing the new cultures to grow to $A_{550}=0.5$. At this point, protein production was induced by the addition of 0.3 mM IPTG. Induced cultures were incubated at 37° C. for 3 hours and centrifuged at 4 000×g and 40° C. for 10 minutes. Pellets were kept at −20 C. for 12 hours, thawed at 4° C. and resuspended with 5 ml of column buffer (10 mM Tris-HCl, pH 7.4, 200 mM NaCl, 1 mM EDTA, 1 mM phenyl-methyl-sulphonyl-fluoride, thereafter "PMSF"), keeping temperature at 4°C. These cell suspensions were sonicated twice at 100 W (20 kHz) for 6 minutes with a 0.5 minute cycle (real time 6 minutes). The whole process was performed in ice. After sonication, samples were kept in ice for 10 minutes and centrifuged at 9 000×g and 4° C. for 30 minutes. Supernatants (soluble intracellular fractions) were recovered and made 1 mM PMSF.

Along with the obtention of soluble intracellular fractions, the amylose resin was equilibrated according to the manufacturer instructions (New England Biolabs, Beverly, USA).

A proportion of 2ml of resin for every 50 ml of original culture was used. The different soluble intracellular fractions were mixed with the equilibrated amylose resin and gently shaked for 12 hours at 4° C. Then, the resin was packed into the same column where equilibration was previously performed (BioRad Laboratories, S.A., Spain) and washed at room temperature with 20 volumes of column buffer at a 6.4 ml/h rate. The fusion protein was eluted with buffer column supplemented with 10 mM maltose. The fractions corresponding to the peak of the fusion protein, determined by absorption at 280 nm, were pooled and stored at 4° C. To test the homogeneity of the fractions, they were resolved in a 10% polyacrylamide/ 0.2% sodium dodecylsulphate (thereafter "SDS") gel electrophoresis.

The expression of the clone carrying the fusion gave rise to the production of a protein with a molecular mass compatible with the one expected. The homogeneity of the preparation was over 95%.

5.F. Obtention of Tbp1 -specific Antibodies, Being the Protein Expressed as in 5.E.

The fusion protein, obtained by the processes described in 5.E. was used as antigen for the generation of polyclonal antibodies against Tbp1. Immunizations were performed as follows: 300 µg of the fusion protein were resuspended with 50 mM potassium phosphate, pH 7.0, 150 mM NaCl (thereafter "PBS") and emulsified with Freund's complete adjuvant (protein solution in PBS/adjuvant solution =1/1). The emulsion was administered subcutaneously to three rabbits (4 months-old New Zealand White females). The rabbits were bleeded previously to the immunization, to obtain preimmune sera. Fifteen and thirty days after the first immunization, 1 mg boost doses in Freund's incomplete adjuvant were administered subcutaneously (protein solution in PBS/adjuvant=1/1). Forty-five days after the first immunization, the rabbits were bleeded by the ear marginal vein. Samples were incubated at 37° C. for 1 hour to allow coagulation. The coagulate was removed from the tube with an sterile Pasteur pipette and sera samples were stored at 4° C. for 12 hours. Then, samples were centrifuged at 1000×g for 30 minutes and supernatants corresponding to sera from each animal were recovered. The serum obtained after immunization with the expression product of pMAL.tr1 will be thereafter named "anti-tr.1".

Study of the Specificity of the Polyclonal Antibodies Generated

Specificity of the sera to Tbp1 from App were tested by ELISA. Outer-membrane extracts of App were used as antigen source and were obtained as follows: *Actinobacillus pleuropneumoniae* was cultured in BHI medium supplemented with 20 µg/ml of NAD to an $A_{660}=0.8$. For Tbp expression, the iron quelator 2-2'-dipyridil was added to 200 µM, and culture was incubated for 3 hours. Then, cultures were centrifuged at 3 000×g for 10 minutes and pellets were resuspended in 10 mM N-2 hydroxyethylpiperazine N-2-ethanesulphonic acid (thereafter "HEPES") and sonicated intermittently at 60 W (real time 90 seconds). Cell debris were removed upon centrifugation at 3 000×g and 4° C. for 10 minutes, and ½ volume of 2% N-laurylsarcosinate sodium salt (thereafter "sarkosyl") was added to the supernatant. After a 10 minute incubation at room temperature, partially-purified outer membranes were pelleted at 100 000×9 and 200 C for 1 hour. Pellets were resuspended in 10 mM HEPES buffer containing ½ volume of 2% sarkosyl. Samples were incubated for 20 minutes at room temperature. The final sarkosyl-insoluble fraction, enriched in outer-membrane proteins, was recovered upon centrifugation at 100 000×g and 20° C. for 1 hour. The pellet was resuspended in 10 mM HEPES buffer and stored at -20° C.

ELISA assays

The response of anti-tr1 sera to App outer-membrane proteins was determined by indirect ELISA. The capacity of the different sera to distinguish among the App serotypes was tested. Thus, double dilutions of the outer-membrane protein preparations from the different serotypes were assayed against a constant 1: 100 dilution of each antiserum. In all cases anti-rabbit antibody coupled to peroxidase was used as second antibody, and DMAB, MBTH and $H_2O_2$ were used as chromogenic substrates. Antisera anti-tr1 recognized a wide range of dilutions of the OMPs from the serotypes tested.

What is claimed is:

1. An isolated and purified nucleotide sequence as set forth in SEQ ID NO:1.

2. A vector comprising the isolated nucleotide sequence of claim 1.

3. The replicative cloning vector of claim 2 wherein said vector is pMAB.tr1 deposited in the CECT (Coleccìon Espanola de Cultivos Tipo) under registration number 4548.

4. An isolated host cell comprising the vector of claim 2.

5. An isolated host cell comprising the vector of claim 3.

6. A process for recombinantly producing a polypeptide comprising culturing the host cell of claim 4 under conditions sufficient for the production of the polypeptide.

7. A process for recombinantly producing a polypeptide comprising culturing the host cell of claim 5 under conditions sufficient for the production of the polypeptide.

* * * * *

SEQUENCE LISTING

```
<160> NUMBER OF SEQ ID NOS:  14

<210> SEQ ID NO 1
<211> LENGTH: 2826
<212> TYPE: DNA
<213> ORGANISM: Actinobacillus pleuropneumoniae
<220> FEATURE:
<221> NAME/KEY: CDS
<222> LOCATION: (11)..(2803)
<221> NAME/KEY: sig_peptide
<222> LOCATION: (11)..(76)
<221> NAME/KEY: mat_peptide
<222> LOCATION: (77)..(2803)

<400> SEQUENCE: 1
ggaatttgct atg aaa aat aaa tta aat ctg att agc ctt gct ctt ctt         49
           Met Lys Asn Lys Leu Asn Leu Ile Ser Leu Ala Leu Leu
               -20                 -15                 -10 agc cta ttt gcc gta caa agc tat gca gaa caa gcg gta caa tta aat        97
Ser Leu Phe Ala Val Gln Ser Tyr Ala Glu Gln Ala Val Gln Leu Asn
                -5              -1   1               5 gat gtt tat gtc aca ggt acc aaa aag aaa gca cat aaa aaa gag aac       145
Asp Val Tyr Val Thr Gly Thr Lys Lys Lys Ala His Lys Lys Glu Asn
         10                  15                  20 gaa gtc aca ggc tta ggg aaa gta gtt aaa aca cca gat act ctt agt       193
Glu Val Thr Gly Leu Gly Lys Val Val Lys Thr Pro Asp Thr Leu Ser
     25                  30                  35 aag gag caa gtg tta gga ata cga gat ctg act cgt tac gac ccc ggt       241
Lys Glu Gln Val Leu Gly Ile Arg Asp Leu Thr Arg Tyr Asp Pro Gly
 40                  45                  50                  55 att tct gtc gta gaa caa ggg aga ggt gcg act aca ggc tac tca att       289
Ile Ser Val Val Glu Gln Gly Arg Gly Ala Thr Thr Gly Tyr Ser Ile
                 60                  65                  70 cgc ggg gta gat cgt aat cgt gtg ggc ttg gca tta gac ggt ttg cca       337
Arg Gly Val Asp Arg Asn Arg Val Gly Leu Ala Leu Asp Gly Leu Pro
             75                  80                  85 cag att caa tcc tat gta agc caa tat tca cgt tcc tca agc ggt gcc       385
Gln Ile Gln Ser Tyr Val Ser Gln Tyr Ser Arg Ser Ser Ser Gly Ala
         90                  95                 100 att aat gaa ata gaa tac gaa aat ctg cgt tcg atc caa att agt aaa       433
Ile Asn Glu Ile Glu Tyr Glu Asn Leu Arg Ser Ile Gln Ile Ser Lys
    105                 110                 115
```

-continued

```
ggg gct agt tct tct gag ttt ggt agt ggc tca cta ggc ggt tcg gtg      481
Gly Ala Ser Ser Ser Glu Phe Gly Ser Gly Ser Leu Gly Gly Ser Val
120             125                 130                 135 caa ttc cgt acc aaa gag gta agc gac att att aag cca ggg caa tct      529
Gln Phe Arg Thr Lys Glu Val Ser Asp Ile Ile Lys Pro Gly Gln Ser
            140                 145                 150 tgg gga tta gat acc aaa agt gcc tac agt agc aaa aat caa caa tgg      577
Trp Gly Leu Asp Thr Lys Ser Ala Tyr Ser Ser Lys Asn Gln Gln Trp
                155                 160                 165 tta aac tca ctt gct ttt gcg ggt act cac aat ggc ttt gat gct ctt      625
Leu Asn Ser Leu Ala Phe Ala Gly Thr His Asn Gly Phe Asp Ala Leu
        170                 175                 180 gtg att tac act cac cgt gat ggt aag gaa acg aaa gct cat aaa gat      673
Val Ile Tyr Thr His Arg Asp Gly Lys Glu Thr Lys Ala His Lys Asp
    185                 190                 195 gca gag agt cgt tct cag aat atc acc cga gta gga gtg gaa acc aac      721
Ala Glu Ser Arg Ser Gln Asn Ile Thr Arg Val Gly Val Glu Thr Asn
200                 205                 210                 215 gag ctt gat acc tca aat aga tat act gcg acg acg aat aat caa cat      769
Glu Leu Asp Thr Ser Asn Arg Tyr Thr Ala Thr Thr Asn Asn Gln His
                220                 225                 230 act tat ggc tgg ttt ttg att aaa gat gaa tgt cca acg tta gat tgt      817
Thr Tyr Gly Trp Phe Leu Ile Lys Asp Glu Cys Pro Thr Leu Asp Cys
            235                 240                 245 acg ccg aaa cag atg gct agg gtg aca aaa gat acg cca tct ttc cgt      865
Thr Pro Lys Gln Met Ala Arg Val Thr Lys Asp Thr Pro Ser Phe Arg
        250                 255                 260 tct tac cct gaa tat act cct gag gaa aaa cag gct tat gag aac caa      913
Ser Tyr Pro Glu Tyr Thr Pro Glu Glu Lys Gln Ala Tyr Glu Asn Gln
    265                 270                 275 aaa cat att aca gag cgt cta aat gct cag gat tac act ggt gaa tat      961
Lys His Ile Thr Glu Arg Leu Asn Ala Gln Asp Tyr Thr Gly Glu Tyr
280                 285                 290                 295 aga gct tta cct gat ccg ctt aaa tat aaa tct gat tct tgg ctg gtt     1009
Arg Ala Leu Pro Asp Pro Leu Lys Tyr Lys Ser Asp Ser Trp Leu Val
                300                 305                 310 aaa tta gga tac aca ttc tct ccg aaa cat tat gtc gct ggt act tat     1057
Lys Leu Gly Tyr Thr Phe Ser Pro Lys His Tyr Val Ala Gly Thr Tyr
            315                 320                 325 gaa cat agc aaa cag cgt tac gac acc cga gat atg acc tat acc gct     1105
Glu His Ser Lys Gln Arg Tyr Asp Thr Arg Asp Met Thr Tyr Thr Ala
        330                 335                 340 tat tgg caa cca tcg gat tta ctt aga act ggt aga aat tgg tat cca     1153
Tyr Trp Gln Pro Ser Asp Leu Leu Arg Thr Gly Arg Asn Trp Tyr Pro
    345                 350                 355 atg aat aat gct aaa gga tta tat cgt gat aat gct tta gat ggt gtt     1201
Met Asn Asn Ala Lys Gly Leu Tyr Arg Asp Asn Ala Leu Asp Gly Val
360                 365                 370                 375 gct att gac tac ttt acg gaa gat ggt gtg aaa tca tca aaa ggt tta     1249
Ala Ile Asp Tyr Phe Thr Glu Asp Gly Val Lys Ser Ser Lys Gly Leu
                380                 385                 390 cgt tgg gca aaa gct cgt ttt att gac gag tgg cac act cgt gat cgc     1297
Arg Trp Ala Lys Ala Arg Phe Ile Asp Glu Trp His Thr Arg Asp Arg
            395                 400                 405 tta ggt gct tta tat cgt tat acc aat caa gat gga aat cgt ctg att     1345
Leu Gly Ala Leu Tyr Arg Tyr Thr Asn Gln Asp Gly Asn Arg Leu Ile
        410                 415                 420
```

-continued

```
gat aga cta tcc ttg agt ttc gat cag caa aaa att aat tta tct acc      1393
Asp Arg Leu Ser Leu Ser Phe Asp Gln Gln Lys Ile Asn Leu Ser Thr
    425                 430                 435 cgc ttg aga gag aac aac tgt tcc gaa tat cca acc ata gat aag aat      1441
Arg Leu Arg Glu Asn Asn Cys Ser Glu Tyr Pro Thr Ile Asp Lys Asn
440                 445                 450                 455 tgc cgt gca act ctt gat aaa ctt tgg tct tca act aaa aat gag caa      1489
Cys Arg Ala Thr Leu Asp Lys Leu Trp Ser Ser Thr Lys Asn Glu Gln
                460                 465                 470 agt tct tat gaa gaa aaa cac gac act att cag ctc tcg tta gat aaa      1537
Ser Ser Tyr Glu Glu Lys His Asp Thr Ile Gln Leu Ser Leu Asp Lys
            475                 480                 485 acc gta caa acg gga ttg ggt aaa cat caa tta aat atg tta tta ggt      1585
Thr Val Gln Thr Gly Leu Gly Lys His Gln Leu Asn Met Leu Leu Gly
        490                 495                 500 tca gac cgt ttc aat tcc acc tta aaa cgc cac gaa att ttg agt gaa      1633
Ser Asp Arg Phe Asn Ser Thr Leu Lys Arg His Glu Ile Leu Ser Glu
    505                 510                 515 ttt tct gtg gga act tgg cat cgt atc aga ggt aac ggt tat aaa gat      1681
Phe Ser Val Gly Thr Trp His Arg Ile Arg Gly Asn Gly Tyr Lys Asp
520                 525                 530                 535 aca cct tac atc tat gag cta aaa gat cag gca att tat agt aaa aat      1729
Thr Pro Tyr Ile Tyr Glu Leu Lys Asp Gln Ala Ile Tyr Ser Lys Asn
                540                 545                 550 gaa tgt gat tat agt ggc act att gca ggt agg gct gat tgt gct aca      1777
Glu Cys Asp Tyr Ser Gly Thr Ile Ala Gly Arg Ala Asp Cys Ala Thr
            555                 560                 565 agt aaa atc aaa ggg cat aat cac tac atc gct ctg aga gat aat ttt      1825
Ser Lys Ile Lys Gly His Asn His Tyr Ile Ala Leu Arg Asp Asn Phe
        570                 575                 580 gcc ata acc aag tat ttg gat att ggt ttg ggt tac cgt ttc gat aag      1873
Ala Ile Thr Lys Tyr Leu Asp Ile Gly Leu Gly Tyr Arg Phe Asp Lys
    585                 590                 595 cat aaa ttc cgt agc act cat cgc tgg gca aat caa ggc gat tat aaa      1921
His Lys Phe Arg Ser Thr His Arg Trp Ala Asn Gln Gly Asp Tyr Lys
600                 605                 610                 615 aac agt gcg tgg aat att ggc ata gtc gca aaa cca acg tca ttc cta      1969
Asn Ser Ala Trp Asn Ile Gly Ile Val Ala Lys Pro Thr Ser Phe Leu
                620                 625                 630 tcg ctc tct tat cga gca tca tct ggc ttt aga gtg cca agt ttc caa      2017
Ser Leu Ser Tyr Arg Ala Ser Ser Gly Phe Arg Val Pro Ser Phe Gln
            635                 640                 645 gag cta ttt ggc tta cgt tat gat ggt gca atg aaa ggc tcc agc gat      2065
Glu Leu Phe Gly Leu Arg Tyr Asp Gly Ala Met Lys Gly Ser Ser Asp
        650                 655                 660 gct tac caa aaa aca gag aag tta tct cct gaa aaa tcc tta aac caa      2113
Ala Tyr Gln Lys Thr Glu Lys Leu Ser Pro Glu Lys Ser Leu Asn Gln
    665                 670                 675 gag gtt gct gcg act ttc aaa ggt gat ttt ggt gtc gtt gaa gtc agt      2161
Glu Val Ala Ala Thr Phe Lys Gly Asp Phe Gly Val Val Glu Val Ser
680                 685                 690                 695 tat ttc aaa aat gac tat aag cag tta att gct cca gca gaa aga atg      2209
Tyr Phe Lys Asn Asp Tyr Lys Gln Leu Ile Ala Pro Ala Glu Arg Met
                700                 705                 710 cat caa act caa tca atg att aac tat ttt aat gtg caa gat att aaa      2257
His Gln Thr Gln Ser Met Ile Asn Tyr Phe Asn Val Gln Asp Ile Lys
            715                 720                 725
```

```
ttg gac ggc att aat ctt att ggt aag cta gat tgg aat ggg gta ttt    2305
Leu Asp Gly Ile Asn Leu Ile Gly Lys Leu Asp Trp Asn Gly Val Phe
        730                 735                 740 gat aaa att cct gag ggc att tac aca aca ttg gct tat agc aaa atg    2353
Asp Lys Ile Pro Glu Gly Ile Tyr Thr Thr Leu Ala Tyr Ser Lys Met
    745                 750                 755 cga gta aaa gag gtg aaa aac tat caa ggg tat atg aat att cgt tct    2401
Arg Val Lys Glu Val Lys Asn Tyr Gln Gly Tyr Met Asn Ile Arg Ser
760                 765                 770                 775 cca ttg tta gat acc att cag cct gct cgc tat gtt gta gga gtg ggg    2449
Pro Leu Leu Asp Thr Ile Gln Pro Ala Arg Tyr Val Val Gly Val Gly
            780                 785                 790 tac gat cag cca gat gaa aaa tgg ggc gtg aat cta aca atg aca cac    2497
Tyr Asp Gln Pro Asp Glu Lys Trp Gly Val Asn Leu Thr Met Thr His
        795                 800                 805 tcc agt gga aaa aat cca aat gag tta aga ggt aat gaa caa gtc ggt    2545
Ser Ser Gly Lys Asn Pro Asn Glu Leu Arg Gly Asn Glu Gln Val Gly
    810                 815                 820 ttt gcc aat tat gag cga act gcc acg aag aaa aga aca ctt tct tgg    2593
Phe Ala Asn Tyr Glu Arg Thr Ala Thr Lys Lys Arg Thr Leu Ser Trp
825                 830                 835 cat acc ttt gac tta acg gga tat atc acc cct tgg aaa cat aca acg    2641
His Thr Phe Asp Leu Thr Gly Tyr Ile Thr Pro Trp Lys His Thr Thr
840                 845                 850                 855 gta cga gct ggc gta tat aac ctg atg aat tat cgt tac acc act tgg    2689
Val Arg Ala Gly Val Tyr Asn Leu Met Asn Tyr Arg Tyr Thr Thr Trp
            860                 865                 870 gaa tcc gta cgt caa tct tcg ctt aat gca att cat cag cat act aac    2737
Glu Ser Val Arg Gln Ser Ser Leu Asn Ala Ile His Gln His Thr Asn
        875                 880                 885 gta aaa gac tat gca agg tat gca gcg ccc ggt aga aat tat gtt gtt    2785
Val Lys Asp Tyr Ala Arg Tyr Ala Ala Pro Gly Arg Asn Tyr Val Val
    890                 895                 900 tca ttc gaa atg aaa ttc taatttagag taccttagtt cta               2826
Ser Phe Glu Met Lys Phe
        905

<210> SEQ ID NO 2
<211> LENGTH: 931
<212> TYPE: PRT
<213> ORGANISM: Actinobacillus pleuropneumoniae

<400> SEQUENCE: 2

Met Lys Asn Lys Leu Asn Leu Ile Ser Leu Ala Leu Leu Ser Leu Phe
        -20                 -15                 -10

Ala Val Gln Ser Tyr Ala Glu Gln Ala Val Gln Leu Asn Asp Val Tyr
    -5                  -1   1               5                  10

Val Thr Gly Thr Lys Lys Ala His Lys Lys Glu Asn Glu Val Thr
                15                  20                  25

Gly Leu Gly Lys Val Val Lys Thr Pro Asp Thr Leu Ser Lys Glu Gln
            30                  35                  40

Val Leu Gly Ile Arg Asp Leu Thr Arg Tyr Asp Pro Gly Ile Ser Val
        45                  50                  55

Val Glu Gln Gly Arg Gly Ala Thr Thr Gly Tyr Ser Ile Arg Gly Val
    60                  65                  70

Asp Arg Asn Arg Val Gly Leu Ala Leu Asp Gly Leu Pro Gln Ile Gln
75                  80                  85                  90
```

-continued

```
Ser Tyr Val Ser Gln Tyr Ser Arg Ser Ser Gly Ala Ile Asn Glu
                 95                 100                 105

Ile Glu Tyr Glu Asn Leu Arg Ser Ile Gln Ile Ser Lys Gly Ala Ser
             110                 115                 120

Ser Ser Glu Phe Gly Ser Gly Ser Leu Gly Gly Ser Val Gln Phe Arg
         125                 130                 135

Thr Lys Glu Val Ser Asp Ile Ile Lys Pro Gly Gln Ser Trp Gly Leu
     140                 145                 150

Asp Thr Lys Ser Ala Tyr Ser Ser Lys Asn Gln Gln Trp Leu Asn Ser
155                 160                 165                 170

Leu Ala Phe Ala Gly Thr His Asn Gly Phe Asp Ala Leu Val Ile Tyr
             175                 180                 185

Thr His Arg Asp Gly Lys Glu Thr Lys Ala His Lys Asp Ala Glu Ser
             190                 195                 200

Arg Ser Gln Asn Ile Thr Arg Val Gly Val Glu Thr Asn Glu Leu Asp
         205                 210                 215

Thr Ser Asn Arg Tyr Thr Ala Thr Thr Asn Asn Gln His Thr Tyr Gly
     220                 225                 230

Trp Phe Leu Ile Lys Asp Glu Cys Pro Thr Leu Asp Cys Thr Pro Lys
235                 240                 245                 250

Gln Met Ala Arg Val Thr Lys Asp Thr Pro Ser Phe Arg Ser Tyr Pro
             255                 260                 265

Glu Tyr Thr Pro Glu Glu Lys Gln Ala Tyr Glu Asn Gln Lys His Ile
             270                 275                 280

Thr Glu Arg Leu Asn Ala Gln Asp Tyr Thr Gly Glu Tyr Arg Ala Leu
         285                 290                 295

Pro Asp Pro Leu Lys Tyr Lys Ser Asp Ser Trp Leu Val Lys Leu Gly
     300                 305                 310

Tyr Thr Phe Ser Pro Lys His Tyr Val Ala Gly Thr Tyr Glu His Ser
315                 320                 325                 330

Lys Gln Arg Tyr Asp Thr Arg Asp Met Thr Tyr Thr Ala Tyr Trp Gln
             335                 340                 345

Pro Ser Asp Leu Leu Arg Thr Gly Arg Asn Trp Tyr Pro Met Asn Asn
         350                 355                 360

Ala Lys Gly Leu Tyr Arg Asp Asn Ala Leu Asp Gly Val Ala Ile Asp
         365                 370                 375

Tyr Phe Thr Glu Asp Gly Val Lys Ser Ser Lys Gly Leu Arg Trp Ala
     380                 385                 390

Lys Ala Arg Phe Ile Asp Glu Trp His Thr Arg Asp Arg Leu Gly Ala
395                 400                 405                 410

Leu Tyr Arg Tyr Thr Asn Gln Asp Gly Asn Arg Leu Ile Asp Arg Leu
             415                 420                 425

Ser Leu Ser Phe Asp Gln Gln Lys Ile Asn Leu Ser Thr Arg Leu Arg
             430                 435                 440

Glu Asn Asn Cys Ser Glu Tyr Pro Thr Ile Asp Lys Asn Cys Arg Ala
         445                 450                 455

Thr Leu Asp Lys Leu Trp Ser Ser Thr Lys Asn Glu Gln Ser Ser Tyr
     460                 465                 470

Glu Glu Lys His Asp Thr Ile Gln Leu Ser Leu Asp Lys Thr Val Gln
475                 480                 485                 490

Thr Gly Leu Gly Lys His Gln Leu Asn Met Leu Leu Gly Ser Asp Arg
             495                 500                 505
```

-continued

```
Phe Asn Ser Thr Leu Lys Arg His Glu Ile Leu Ser Glu Phe Ser Val
            510                 515                 520
Gly Thr Trp His Arg Ile Arg Gly Asn Gly Tyr Lys Asp Thr Pro Tyr
        525                 530                 535
Ile Tyr Glu Leu Lys Asp Gln Ala Ile Tyr Ser Lys Asn Glu Cys Asp
    540                 545                 550
Tyr Ser Gly Thr Ile Ala Gly Arg Ala Asp Cys Ala Thr Ser Lys Ile
555                 560                 565                 570
Lys Gly His Asn His Tyr Ile Ala Leu Arg Asp Asn Phe Ala Ile Thr
                575                 580                 585
Lys Tyr Leu Asp Ile Gly Leu Gly Tyr Arg Phe Asp Lys His Lys Phe
            590                 595                 600
Arg Ser Thr His Arg Trp Ala Asn Gln Gly Asp Tyr Lys Asn Ser Ala
        605                 610                 615
Trp Asn Ile Gly Ile Val Ala Lys Pro Thr Ser Phe Leu Ser Leu Ser
    620                 625                 630
Tyr Arg Ala Ser Ser Gly Phe Arg Val Pro Ser Phe Gln Glu Leu Phe
635                 640                 645                 650
Gly Leu Arg Tyr Asp Gly Ala Met Lys Gly Ser Ser Asp Ala Tyr Gln
                655                 660                 665
Lys Thr Glu Lys Leu Ser Pro Glu Lys Ser Leu Asn Gln Glu Val Ala
            670                 675                 680
Ala Thr Phe Lys Gly Asp Phe Gly Val Val Glu Val Ser Tyr Phe Lys
        685                 690                 695
Asn Asp Tyr Lys Gln Leu Ile Ala Pro Ala Glu Arg Met His Gln Thr
    700                 705                 710
Gln Ser Met Ile Asn Tyr Phe Asn Val Gln Asp Ile Lys Leu Asp Gly
715                 720                 725                 730
Ile Asn Leu Ile Gly Lys Leu Asp Trp Asn Gly Val Phe Asp Lys Ile
                735                 740                 745
Pro Glu Gly Ile Tyr Thr Thr Leu Ala Tyr Ser Lys Met Arg Val Lys
            750                 755                 760
Glu Val Lys Asn Tyr Gln Gly Tyr Met Asn Ile Arg Ser Pro Leu Leu
        765                 770                 775
Asp Thr Ile Gln Pro Ala Arg Tyr Val Val Gly Val Gly Tyr Asp Gln
    780                 785                 790
Pro Asp Glu Lys Trp Gly Val Asn Leu Thr Met Thr His Ser Ser Gly
795                 800                 805                 810
Lys Asn Pro Asn Glu Leu Arg Gly Asn Glu Gln Val Gly Phe Ala Asn
                815                 820                 825
Tyr Glu Arg Thr Ala Thr Lys Lys Arg Thr Leu Ser Trp His Thr Phe
            830                 835                 840
Asp Leu Thr Gly Tyr Ile Thr Pro Trp Lys His Thr Thr Val Arg Ala
        845                 850                 855
Gly Val Tyr Asn Leu Met Asn Tyr Arg Tyr Thr Thr Trp Glu Ser Val
    860                 865                 870
Arg Gln Ser Ser Leu Asn Ala Ile His Gln His Thr Asn Val Lys Asp
875                 880                 885                 890
Tyr Ala Arg Tyr Ala Ala Pro Gly Arg Asn Tyr Val Val Ser Phe Glu
                895                 900                 905
Met Lys Phe
```

```
<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 3
gggcttggca ttagacggtt tgcc                                          24

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4
ggcggttcgg tgcaattccg                                               20

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 5
gcgggtactc acaatggctt tgatgctc                                      28

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 6
cccgagtagg agtggaaacc aacgag                                        26

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 7
gcgtctaaat gctcaggatt acactggtg                                     29

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 8
cagttgttct ctctcaagcg ggtag                                         25

<210> SEQ ID NO 9
<211> LENGTH: 20
<212> TYPE: DNA
<213> ORGANISM: Artificial Sequence
<220> FEATURE:
```

```
<223> OTHER INFORMATION: Description of Artificial Sequence: Primer

<400> SEQUENCE: 9
gtagcacaat cagccctacc                                              20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 10
gcccagcgat gagtgctacg g                                            21

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 11
cgtcattcct atcgctctct tatcgag                                      27

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 12
gttgtaggag tggggtacta tcagcc                                       26

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 13
gctatgcaga attcgcggta caattaaatg                                   30

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 14
ggtactctag attagaattt catttc                                       26
```